(12) United States Patent
Pond

(10) Patent No.: US 7,029,278 B2
(45) Date of Patent: Apr. 18, 2006

(54) HANDHELD DEVICE FOR APPLYING DENTAL MATERIALS

(76) Inventor: Gary J. Pond, 2816 N. Main St., Racine, WI (US) 53402

( * ) Notice: Subject to any disclaimer, the term of this patent is extended or adjusted under 35 U.S.C. 154(b) by 192 days.

(21) Appl. No.: 10/667,164

(22) Filed: Sep. 17, 2003

(65) Prior Publication Data
US 2004/0106083 A1 Jun. 3, 2004

Related U.S. Application Data

(60) Provisional application No. 60/411,297, filed on Sep. 17, 2002.

(51) Int. Cl.
*A61C 3/06* (2006.01)
*A61C 1/12* (2006.01)
(52) U.S. Cl. .................................... 433/125; 433/82
(58) Field of Classification Search .................. 433/82, 433/84, 85, 87, 125; 15/24, 31; 401/138, 401/179
See application file for complete search history.

(56) References Cited

U.S. PATENT DOCUMENTS

| 3,389,468 | A | | 6/1968 | Lewis et al. |
| 3,775,849 | A | * | 12/1973 | Condon ..................... 433/87 |
| 3,826,004 | A | * | 7/1974 | Graceffo ..................... 433/85 |
| 4,220,446 | A | * | 9/1980 | Walker ..................... 433/85 |
| 5,642,994 | A | * | 7/1997 | Chipian et al. ............ 433/82 |
| 5,779,708 | A | | 7/1998 | Wu |
| 5,927,976 | A | | 7/1999 | Wu |
| 6,083,000 | A | | 7/2000 | Charlton |

\* cited by examiner

*Primary Examiner*—Todd E. Manahan
(74) *Attorney, Agent, or Firm*—Ryan Kromolz & Manion, S.C.

(57) ABSTRACT

A dental handpiece for applying dental material to polish a tooth. The handpiece includes a conduit and a plunger for dispensing dental material adjacent a polishing member. The plunger and the polishing member can be controlled by a drive member, which may move in both a forward and reverse direction.

7 Claims, 3 Drawing Sheets

HANDHELD DEVICE FOR APPLYING DENTAL MATERIALS

RELATED APPLICATION

This application claims the benefit of co-pending provisional patent application Serial No. 60/411,297, filed 17 Sep. 2002.

BACKGROUND OF THE INVENTION

The present invention relates generally to a dental handpiece, and more specifically to a dental handpiece adapted to apply dental material to a patient's tooth or teeth and having removable sections.

Dental handpieces for dispensing dental material are well known in the art. For example Charlton (U.S. Pat. No. 6,083,000) and Lewis (U.S. Pat. No. 3,389,3468) are designed to distribute dental material in a controlled fashion. Generally, a predetermined amount of dental material is stored in a reservoir within the handpiece and a longitudinally moving plunger pushes a plug into the reservoir, dispensing the dental material in a controlled fashion. The dental material may be loaded directly within the reservoir or contained within a capsule that is placed within the reservoir.

Although dental handpieces and disposable capsules have become a convenient way to dispense a controlled amount of dental material into a patient's mouth, the handpieces do not necessarily provide the most sterile environment. Though capsules of dental material can be measured for a single patient use, there still may be residue dental material in the handpiece itself after use. Especially when a corkscrew style plunger is used, the handpiece may not be sufficiently cleaned or sterilized between consecutive patients. The dental material is not easily washed out of the devices, and one cannot be certain that the material has been completely removed.

For the foregoing reasons, there is a need for a device that will allow a dentist, hygienist, or a dental assistant to dispense a controlled amount of dental material into a patient's mouth in a manner that is efficient and hygienic.

SUMMARY OF THE INVENTION

The present invention alleviates the above problem by disclosing a dental handpiece that is easily kept clean and sterile. The handpiece is designed generally to dispense prophy paste or similar material in a safe, sanitary manner.

The handpiece comprises a detachable shield that fits securely onto the body of the handpiece. The shield contains a conduit passing through the shield. At one end the conduit is in fluid communication with a reservoir of dental material, and the opposing end of the conduit is in fluid communication with the area where the dental material will be dispensed. Once the shield has been used, it may be removed and discarded, or autoclaved if preferred. The disposable shield helps ensure that residual dental material will not pass from one application to the next.

Along with the shield, the reservoir for the dental material contributes to the sanitary nature of the invention. The reservoir is adapted to receive a cartridge of dental material having opposing ends. One end of the capsule is in fluid communication with a conduit located in the shield, while the opposite end is in communication with a plunger. The plunger pushes the dental material through the reservoir so that the dental material may enter the conduit located in the shield. Because of the design of the reservoir, plunger, and the cartridge, the dental material has minimal contact with the walls of the reservoir, and the cartridge may be discarded after being used, thereby contributing to the overall sanitary features of the handpiece. Likewise, the design prevents dental material from coming in contact with any of the mechanical parts of the handpiece.

The plunger pushes the dental material through the conduit in the shield, allowing the material to exit at an area where a tooth is to be polished by a rotating polishing device, such as a prophy cup.

The plunger can be operated manually, but is preferably driven by a drive mechanism located within the body of the handpiece. The plunger has a semi-helical design, which meshes with a gear or cog connected to the drive mechanism. The drive mechanism also drives the polishing device or other attachment located on the end of the handpiece. A reversible direction trigger controls the drive mechanism, allowing easy control of the handpiece. The drive mechanism is enclosed within the body of the handpiece and does not come into contact with the dental material.

The overall design allows for an efficient dental handpiece with improved sanitary operating conditions. Dental material will generally be completely removed after each application, and the mechanical features of the device will not come into contact with the dental material.

These and other advantages will become more evident in the following description.

DETAILED DESCRIPTION

Although the disclosure hereof is detailed and exact to enable those skilled in the art to practice the invention, the physical embodiments herein disclosed merely exemplify the invention that may be embodied in other specific structures. While the preferred embodiment has been described, the details may be changed without departing from the invention, which is defined by the claims.

Figure 1:
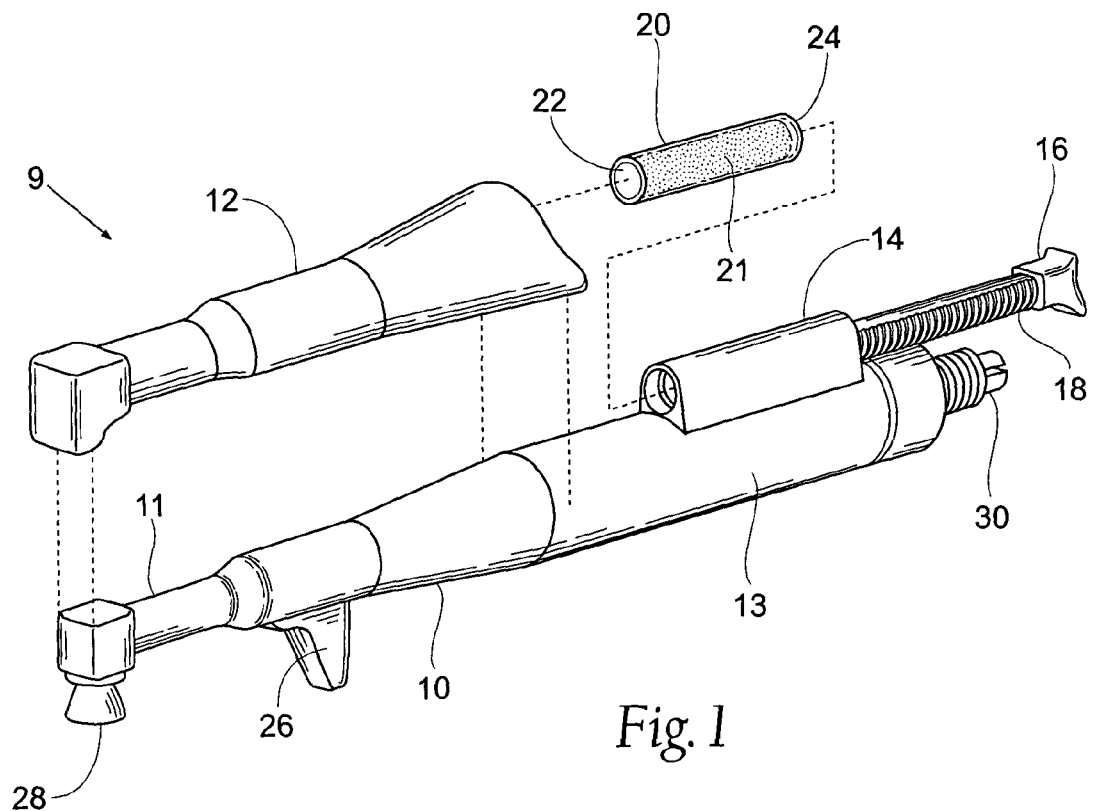
FIG. 1 is an exploded perspective view of an embodiment of the current invention.

FIG. 1 shows an exploded view of a handpiece 9 in accordance with the present invention. The handpiece 9 has a body 10 that allows a user to engage the handpiece 9. A removable shield 12 fits securely onto a front portion 11 of the body 10. A reservoir 14 sits on a back portion 13 of the body 10. The reservoir 14 and the body may be formed from one piece of material or separate pieces. The reservoir 14 is in communication with a plunger 16 having a helical underside 18. The reservoir 14 will also contain a through cartridge 20 containing a dental material or prophy paste 21. The cartridge 20 has a first end 22 and a second end 24. The first end 22 can be sealed, while the second end 24 is generally open. The second end 24 may contain a removable cover (not shown) for when the cartridge 20 is not in use. A trigger device 26 is connected to the body 10 and can control the action of a polishing member 28. An adaptor 30 allows the handpiece 9 to be powered from a power source, preferable an air source, but any suitable power source will be allowed (not shown).

Figure 2:
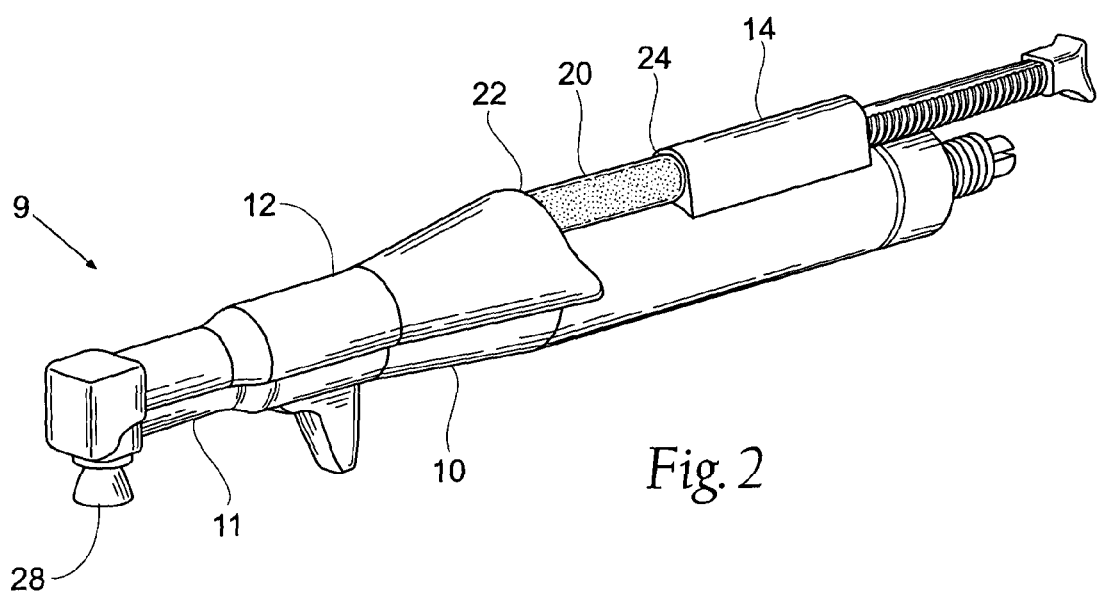
FIG. 2 is a perspective view of an embodiment of the current invention.

FIG. 2 shows a perspective view of the handpiece 9 of the present invention. The shield 12 fittingly sits on the front end 11 of the body 10 and protects the body 10 from undue splatter when the polishing member 28 is in use. The cartridge 20 fits securely between the reservoir 14 and the shield 12, with a portion of the cartridge 20 secured inside of the reservoir 14. Generally, the cartridge 20 will be secured in the handpiece 9 before the shield 12 is secured on the handpiece 9. The opposing ends 22 and 24 are in fluid communication with the shield 12 and the reservoir 14, respectively. This communication can be seen clearer in FIG. 3.

Figure 3:
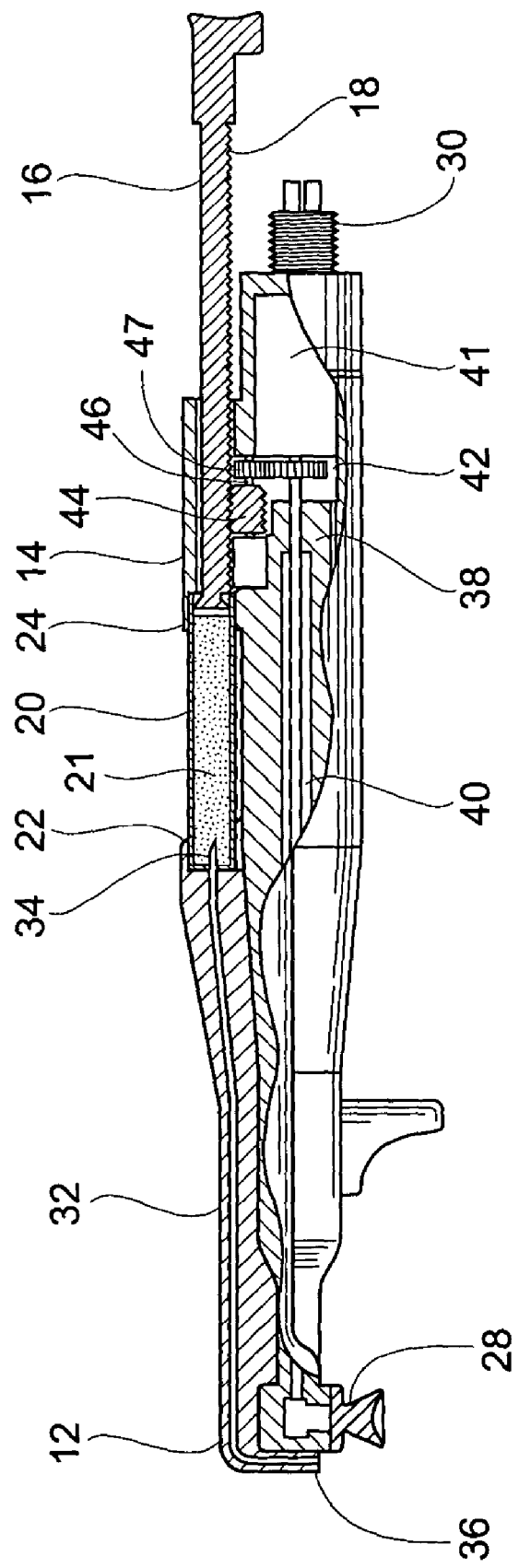
FIG. 3 is a cutaway view of the invention shown in FIG. 2.

FIG. 3 is a sectional view of the handpiece 9. The shield 12 has a through conduit 32 having a proximal end 34 and a distal end 36. The distal end 36 is located near the polishing member 28 and allows an exit for the dental material 21. The proximal end 34 is in fluid communication with the first end 22 of the cartridge 20. The proximal end 34 is sharpened so that it can pierce and penetrate the closed first end 22 of the cartridge 20. This ensures that the dental material 21 will only be delivered into the conduit 32 of the shield, rather into or onto the handpiece 9. As a safety measure, the proximal end 34 preferably does not extend past the end of the shield 12.

Still referring to FIG. 3, the second end 24 of the cartridge 20 is secured within the reservoir 14. The cartridge 20 is shown protruding out of the reservoir 14, but it is possible that the reservoir 14 would encompass most or the entire cartridge 20. The second end 24 is arranged so that it will be able to receive the plunger 16. The helical underside 18 of the plunger 16 is in contact with a threaded cog 44. The helical underside 18 meshes with the cog 44, and as the cog 44 turns, the plunger 16 is moved forward to engage the dental material 21 within the cartridge 20. If the plunger 16 is to be withdrawn, the cog 44 is rotated in the opposite direction and the plunger 16 moves backward. While the design of the plunger 16 allows it to move backward and forward without rotating, it is also conceivable that the plunger 16 may be designed to rotate.

Essentially a drive mechanism 38 drives the cog 44. The drive mechanism 38 consists of a main drive shaft 40, a motor 41, a main drive gear 42, a secondary drive shaft 46, and a secondary drive gear 47. The drive mechanism 38 receives power through the adaptor 30, which can be joined to any suitable power source. Ideally, the device is driven with air as a power source, but any suitable power source is allowable.

The motor 41 turns the main drive gear 42. The teeth of the main drive gear 42 mesh with the teeth of the secondary drive gear 47. The main drive gear 42 will turn, thereby rotating the secondary drive gear 47, causing the secondary drive shaft 46 to rotate, as well. The secondary drive shaft 46 turns the cog 44, thereby moving the plunger 16, as stated above.

The main drive shaft 40 is connected to the polishing means 28. As the motor 41 turns the main drive gear 42, the main drive shaft 40 is also turned, thereby spinning the polishing means 28. In a preferred embodiment, the polishing means 28 is a prophy cup. The handpiece 9 is designed so that the polishing means 28 and the plunger 16 are rotated or moved concurrently, thereby allowing the user to manipulate a single control to polish a patient's tooth.

Figure 4:
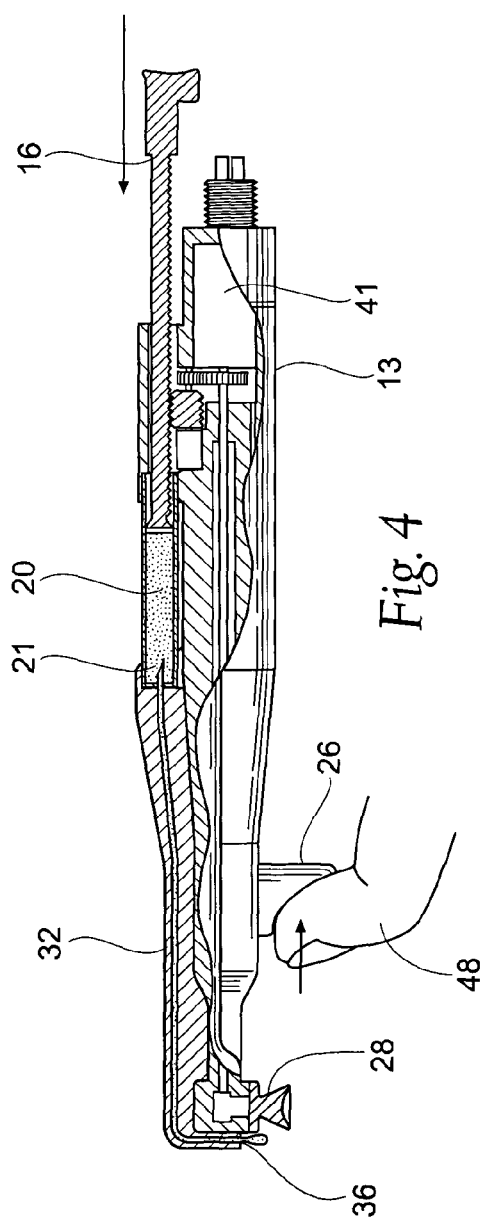
FIG. 4 shows a cutaway view of the present invention in use by a person.
Figure 5:
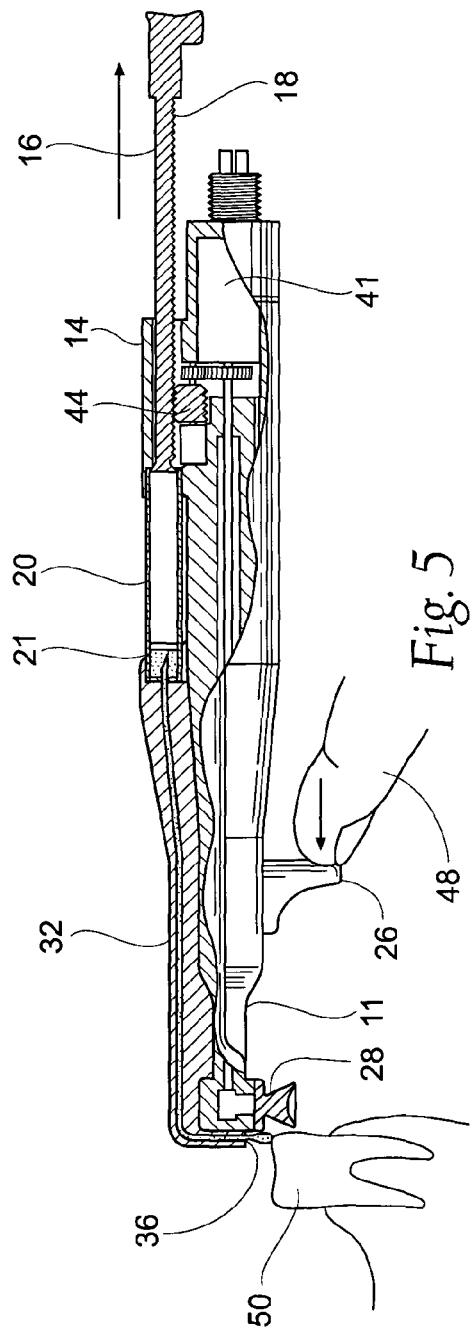
FIG. 5 shows a cutaway view of the present invention after a user has finished applying a dental material.

Referring to FIGS. 4, 5, and 6, the handpiece 9 is shown engaged by a finger 48. The finger 48 makes contact with the trigger 26. The trigger is connected to and controls the motor 41, thereby controlling the drive mechanism 38. The trigger 26 allows for both a forward and reverse direction of the drive mechanism 38. As shown in FIG. 4, the drive mechanism 38 is activated by pulling the trigger 26 backwards toward the back portion 13 of the handpiece 9, allowing the plunger 16 to move forward and into the reservoir 14, contacting the cartridge 20 of dental material 21. The dental material 21 passes through the conduit 32 and exits at the distal end 36 of the conduit 32. The dental material 21 can then be deposited on a tooth 50 (see FIG. 6), which will be polished by the polishing means 28. If one wishes to stop the flow of dental material 21, one simply removes their finger from the trigger 26.

When the polishing is finished, the trigger 26 can be moved in the opposite direction towards the front portion 11 of the handpiece 9, as shown in FIG. 5, thereby causing the plunger 16 to withdraw from the reservoir 14 and the cartridge 20. The empty cartridge 20 may then be removed from the handpiece 9 and discarded. It is also possible that the plunger 16 may be designed so that one could manually disengage the helical side 18 of the plunger 16 from the cog 44 and be removed from the reservoir 14 manually. The cartridge 20 and the shield 12 are then discarded, or autoclaved if desired. The result is a polished tooth 50 and a handpiece 9 without residual dental material 21 built up on the handpiece 9.

While the drive mechanism 38 is described to control both the polishing means 28 and the plunger 16, it is foreseeable that they could be operated by separate controls. Also, if desired, the plunger 16 could be operated manually rather than by a motor, and the movement of the plunger 16 could also control the polishing means 28 without use of a motor.

The foregoing is considered as illustrative only of the principles of the invention. Furthermore, since numerous modifications and changes will readily occur to those skilled in the art, it is not desired to limit the invention to the exact construction and operation shown and described. While the preferred embodiment has been described, the details may be changed without departing from the invention, which is defined by the claims.

What is claimed is:

1. A dental handpiece arranged for delivery of a dental material comprising:
   a generally hollow body, said body allowing engagement of the handpiece;
   a reservoir containing said dental material, said reservoir securely attached to said body;
   a plunger, said plunger able to penetrate said reservoir, said plunger in communication with said dental material;
   a polishing member located near said distal end of said through conduit; and
   a drive member connected to said polishing member;
   a removable shield; and
   a through conduit located in said shield, said conduit having a proximal end and a distal end, said proximal end in fluid communication with said reservoir and said distal end in fluid communication with an area wherein said dental material may be applied.

2. The device according to claim 1 wherein said dental material in said reservoir is contained in a removable cartridge.

3. The device according to claim 2 wherein said dental material comprises a prophy paste.

4. The device according to claim 1 further comprising a control mechanism for said drive member.

5. The device according to claim 4 wherein the control mechanism is a reversible trigger.

6. The device according to claim 1 wherein said shield is autoclavable.

7. A dental handpiece arranged for delivery of a dental material comprising:
- a generally hollow body, said body allowing engagement of the handpiece;
- a reservoir securely attached to said body, said reservoir having an open area for insertion of a removable cartridge of dental material;
- a plunger, said plunger able to penetrate said reservoir, said plunger in communication with said dental material;
- a polishing member located near said distal end of said through conduit; and
- a drive member connected to said polishing member and said polishing member;
- a control mechanism fro said drive member;
- a removable shield; and
- a through conduit located in said shield, said conduit having a proximal end and a distal end, said proximal end in fluid communication with said reservoir and said distal end in fluid communication with an area wherein said dental material may be applied.

* * * * *